United States Patent [19]

Jo et al.

[11] Patent Number: 4,785,794

[45] Date of Patent: Nov. 22, 1988

[54] METHOD FOR PROCESSING AQUEOUS SUGAR JUICE FOR SEPARATING KETOSE

[75] Inventors: Louis F. Jo; Marie E. Borredon, both of Toulouse; Michel Delmas, Auzeville; Antoine Gaset, Toulouse, all of France

[73] Assignee: Institut National Polytechnique de Toulouse, Toulouse, France

[21] Appl. No.: 4,451

[22] Filed: Jan. 20, 1987

[30] Foreign Application Priority Data

Jan. 17, 1986 [FR] France ................. 86 01123

[51] Int. Cl.$^4$ .............. C13D 3/00; C13D 3/12; C13K 11/00
[52] U.S. Cl. ............... 127/46.1; 127/55; 127/48; 426/658; 549/476; 536/127
[58] Field of Search ........... 127/46.1, 46.2, 55, 127/48; 426/658, 271; 549/476; 536/124, 127

[56] References Cited

U.S. PATENT DOCUMENTS

| | | | |
|---|---|---|---|
| 3,290,263 | 12/1966 | Smythe et al. | 536/124 |
| 3,533,839 | 10/1970 | Hara et al. | 127/46.1 |
| 4,663,449 | 5/1987 | Barker et al. | 536/124 |

FOREIGN PATENT DOCUMENTS

| | | | |
|---|---|---|---|
| 428617 | 1/1967 | Japan. | |
| 1174 | 1/1971 | Japan | 127/46.1 |
| 119964 | 6/1975 | Japan | 127/58 |

OTHER PUBLICATIONS

Chemical Abstracts, vol. 67, No. 108947m; 1967.
"Preparation of Furan Derivatives From Pentoses And Hexoses"; 1982; J. S. Ballesteros et al; Bull. Chim. Fr., pp. 176–180.
"Reactions of Monosaccharides With Beta-Ketonic Esters"; 1956; pp. 98–141; F. G. Gonzalez, Adv. Carbohydr. Chim.

Primary Examiner—Helen M. S. Sneed
Assistant Examiner—Chung K. Pak
Attorney, Agent, or Firm—Harold H. Dutton, Jr.

[57] ABSTRACT

A method for processing aqueous sugar juice containing a mixture of aldehyde-function saccharides and ketonic-function saccharides for separating and selecting ketonic-function saccharides, comprising (a) producing a hydro-organic medium by mixing the juice with an active methylene ketonic compound, a calcium-based catalyst and preferably ethanol, (b) mixing the medium until furanic polyalcohol is formed by condensation of the ketonic compound and the aldehyde-function saccharides and (c) allowing the furanic polyalcohol to precipitate and separating it by physical means from the liquid medium.

11 Claims, No Drawings

METHOD FOR PROCESSING AQUEOUS SUGAR JUICE FOR SEPARATING KETOSE

BACKGROUND OF THE INVENTION

1. Field of the Invention

This invention relates to a method for processing aqueous sugared juice containing a mixture of at least one aldehyde-function saccharide (aldose) and at least one ketonic-function saccharide (ketose). It is intended to separate and select the ketonic-function saccharides and to eliminate the aldehyde-function saccharides in the form of useable by-products. The invention is especially applicable to aqueous fructose and glucose mixtures with a view to obtaining glucose-free fructose syrups.

2. Description of Related Art

It is common knowledge that in the sugar and starch industries, as in the canning industries, the pressing juice from sacchariferous plants or the effluents from the various transformations of the basic products result directly or indirectly in mixtures of aldehydic saccharides and ketonic saccharides, mainly glucose and fructose.

When sufficiently concentrated, these mixtures are used either for foodstuffs or, recently, in certain industrial sectors (precision chemistry).

In these mixtures, the glucose has an annoying effect, both industrially, as it conditions parasitic reactions in the subsequent processes, and in the area of foodstuffs, in which it considerably increases the calory-content of the fructose syrups manufactured from the sugared juices.

Of the two main methods for separating the glucose from fructose syrups, one uses chromatographic techniques. The major drawback of these processes is in their very high operating cost. Moreover, the fractional crystallization techniques only apply to very fructose-rich syrups that need to be purified.

The present invention provides a new method for separating aldehyde-function saccharides from ketone-function saccharides.

A primary object of this invention is to provide a moderately priced method applicable both to concentrated juices and more diluted juices (from sugar works, starch works, canning effluents etc.) in order to obtain ketonic saccharide solutions of edible quality.

Another object is to enable the valorization of the aldehydic saccharides to be eliminated by transforming them into a product useable in various industrial fields, especially as a base product for manufacturing polymers.

A further object is to obtain very pure ketonic saccharide syrups, especially fructose.

To this end, the method according to the present invention for processing an aqueous sugar juice containing a mixture of at least one aldehyde-function saccharide and at least one ketonic-function saccharide for separating and selecting the ketonic-function saccharides, comprises in a combination:

(a) producing a reactive hydro-organic medium by mixing the sugared juice with a reagent comprising at least one active methylene ketonic compound and a calcium-based catalytic reagent (referred to below as the catalyst), (b) mixing the medium for enhancing contact between the phases enabling the condensation of the ketonic compound and the aldehyde-function saccharides with the formation of furanic polyalcohol, (c) allowing the furanic polyalcohol to precipitate in the reactive medium and separating it by physical means from the liquid medium containing the ketonic-function saccharides.

It was observed that the formation of condensation was greatly improved when the hydro-organic medium contained ethanol or methanol, which would, in a preferred embodiment, be added to the medium in the course of operation (a). So, no degradation product pollutes the medium after the reaction.

Thus, the work of the present inventors revealed a condensation reaction which, unexpectedly, had the remarkable property of being totally selective with respect to aldehydic saccharides: in a hydro-organic medium (in a preferred embodiment, water with ethanol or methanol) and in the presence of a calcium-based catalyst, this reaction subjects the aldehydic saccharides, and, in particular, the glucose, to a stoichiometric transformation, and maintains in their entirety the ketonic saccharides and especially the fructose. The aldehydic saccharides are transformed into furanic polyalcohols without a secondary reaction: this body precipitates spontaneously in the hydro-organic reactive medium and so may be separated off, in particular by simple filtration, to produce a liquid phase containing only the ketonicfunction saccharides.

According to a preferred embodiment, the hydro-organic medium is produced by adjusting the quantity of alcohol with respect to the quantity of water, so that the relative proportional content of alcohol in the water is approximately between 80 and 95%. Moreover, in a preferred embodiment, the solvent used is ethanol. These conditions ensure a very high separating efficiency (generally greater than 95%), and enable a ketonic saccharide solution of edible quality to be obtained.

In a preferred embodiment, the active methylene ketonic compound is mixed slightly in excess of the stoichiometric proportions with respect to the aldehyde-function saccharides contained in the sugar juice in order to obtain a total transformation of these aldehydic saccharides into furanic polyalcohol. Furthermore, the calcium-based catalyst, in particular the calcium chloride, may be mixed in molar proportions of between 1 and 6 with respect to the aldehyde-function saccharides contained in the sugared juice.

The ketonic reagent comprises in particular ethyl or methyl acetylacetate or acetylacetone, which have the advantage of being of a non-toxic character in the event of residual traces.

In order to reduce the duration of the reaction, the reactive medium should be heated to a temperature between 40° C. and the reflux temperature of the reactive medium for a duration of between about four to eight hours, In practice, a temperature in the immediate vicinity of the solvent reflux temperature, in particular 78° C. in the case of ethanol (reflux of ethanol/water azeotrope) could be adopted.

The precipitation of the polyalcohol, in a preferred embodiment, takes place cold and may be enhanced by adding water to the medium after the condensation reaction.

The advantage of the method of separation in compliance with the present invention, which produces totally aldehydic saccharide-free ketonic saccharide syrups, can be easily appreciated. These syrups lend themselves to an industrial or food stuff application without parasitic reactions generating toxic products and without the penalizing calory content caused by the presence of glucose.

It is to be noted that laboratory studies have already been carried out as to the condensation reaction of pure glucose (or other pure aldehydic sugars) with the aim of synthesizing furanic polyalcohols. Reference may be made to the following publications which mention this reaction: F. J. LOPEZ APARICIO et al, Carbohydrate Research, vol. 107, 1982, pages 292–295; F. GARCIA-GONZALEZ, Adv. Carbohydr. Chim. 1956, 11, p. 111; J. S. BALLESTEROS, D. J. MCPHEE, D. HERNANDEZ, Bull. Soc. Chim. FR 1982, p 176; M. OKADA, Y. KASHIWABARA, T. IMAMURA, M. YAMADA, M. KAKEHI; Chemical 35 Abstracts, 1967, 67, n°, 108947 M.

Nevertheless, these studies were aimed at solely a condensation reaction of pure samples in a synthetic medium and not a separation of one variety in a mixture, and describe or suggest no selective property as to this reaction. On the contrary, these publications, and notably the first mentioned, show that under the operating conditions and given the catalysts used, the condensation reaction affects indiscriminately both glucose and fructose. They thus provide no information directly applicable to solving the problem of separation, subject of the present invention. Furthermore, these studies recommend particular application conditions or specific type of catalyst (Lewis acids, notably $ZnCl_2$) which are difficult to exploit industrially due to the serious problems which result: random reproducibility, metal contamination during the aqueous phases, difficulties collecting the furanic polyalcohols which crystallize poorly, maximum output (approx. 60%).

DESCRIPTION OF PREFERRED EMBODIMENTS

The examples which follow illustrate the separation process according to the invention.

EXAMPLE 1

100 g of sucrose (cane sugar) are hydrolized by 46 g of "Amberlit E 252" cationic resin as sold by the "Rohm and Haas" company. This reaction takes place in 50 ml of water and 160 ml of ethanol at 80° C.

After separating the resin from the reactive medium and titrating the quantity of glucose contained in the solution, 93 ml of this solution containing 18 g of glucose is mixed with 7 ml of ethanol, 55 g of calcium chloride and 26.5 ml of ethyl acetylacetate.

The medium is mixed and heated at 78° C. (reflux temperature) for six and a half hours.

During the reaction, a precipitation of whitish crystals may be observed. At the end of the reaction, 400 ml of water are added and the crystals filtered.

The pregnant solution is left at rest. Then a further filtration of this solution is performed to allow 4-(D-arabino-tetroxybutyl) 2-methyl-5 ethylfuroate crystals to be collected once more.

The resulting filtrate is subjected to two purification stages: extraction of the ethanol from the medium by slow distillation, and extraction of the excess ethyl acetylacetate by the ethyl acetate for recycling; simultaneous demineralization and decoloring by ion exchangers (Lewatit SP 102/MP 64 sold by the BAYER company).

The resulting solution is dehydrated and gives pure fructose syrup with a fructose content greater than 95% by weight, free of ethyl acetylacetate, salt and ethanol.

The fructose crystallizes upon addition of ethanol to the resulting syrup.

EXAMPLE 2

The hydrolysis is performed according to Example 1 but with no addition of ethanol: the initial concentration of sucrose is of 32.4 g for 100 ml of water. After hydrolysis, the medium is concentrated until a sugar syrup is obtained and, for 18 g of glucose, 30 g of calcium chloride are added, then, by using a bromine funnel, 9 ml of acetylacetone are added.

This medium is heated at 80° C. for five hours and the resulting furanic crystals are filtered off and then purified giving acetyl-4-(D-arabino-tetroxybutyl)-2-methyl-5-furan.

The resulting filtrate is subjected to demineralization giving at the end of the operation a fructose syrup containing 60% fructose by weight. However a deterioration of the glucose may be observed which produces a certain degree of contamination of the syrup, requiring a specific purification. An alcoholic organic medium will thus be used in a preferred embodiment.

EXAMPLE 3

In this example, cane sugar molasses, for which the saccharide content varies from 39 to 61%, are process.

100 g of cane sugar molasses are placed in a reactor. Hydrochloric acid is then added until pH=2. The mixture is heated to 85° C. for about half an hour. The inversion is controlled by high performance liquid chromatography (H.P.L.C.). The mixture is neutralized by the slow addition of lime (pH 6–7).

After inversion, the method of the invention is applies: calcium chloride (12 g for 10 g of saccharides) and 23 g of methyl acetylacetate for 18 g of glucose, then 150 ml of ethanol, are added.

The mixture is heated at 78° C. for six and a half hours, 200 ml of water are added at the end of the reaction and the furanic crystals so formed are separated from the pregnant solution in order to give methyl-4-(D-arabino tetroxybutyl) 2-methyl-5 furoate.

A pure fructose syrup is obtained with a 90% fructose content.

EXAMPLE 4

In this example, beet sugar molasses, for which the total saccharide content varies from 37 to 75% by weight, are processed.

The inversion is carried out using hydrochloric acid (8 ml at 33%) added to 100 g of sugar beet molasses.

The mixture is heated to 80° C. The sucrose-to-glucose and fructose conversion rate is controlled by "H.P.L.C."

Once the medium is neutralized, the calcium chloride is added (12 g for 10 g of saccharides), then the ethyl acetylacetate (26 g for 18 g of glucose), finally 150 ml of ethanol are added.

The mixture heated to 78° C. is stirred for six and a half hours, then the water is added to produce ethyl-4-(D-arabino-tetroxybutyl) 2-methyl-5-furoate after several recrystallizations.

After crystallization and filtering, the foregoing filtrate is purified in a manner similar to Example 1 in order to produce pure fructose syrup with a fructose content of 93%.

EXAMPLE 5

80 ml of ethanol, 55.5 g of calcium chloride and 31.64 g of butyl acetylacetate are added to a mixture of aldehyde and ketonic-function saccharides containing 18 g of glucose for 20 ml of water.

The reactive medium is warmed to the water-ethanol azeotropic reflux (78° C.) for six and a half hours and results in the formation of ethyl-4-(D-arabino-tetroxybutyl)2-propyl-5 furoate.

The ethanol and the B diketone are extracted from the filtrate; the latter then has the catalyst removed.

The fructose syrup so obtained has a 90% fructose content by weight.

EXAMPLE 6

A fraction of invert sugar syrup with a glucose content of 900 g/l is added to 80 ml of ethanol, 55.5 g of calcium chloride and 38.4 g of ethyl benzoylacetate.

The mixture is heated at 78° C. for six and a half hours to produce ethyl-3-(D-arabino-tetroxybutyl)5-phenyl-2 furoate.

The filtrate recovered is purified to produce a fructose syrup with 70% content by weight.

While this invention has been described as having preferred features and embodiments, it will be understood that it is capable of still further modification and adaptation within the spirit of the invention, and this application is intended to cover all variations, adaptations, modifications and alternatives as may fall within the spirit of the invention and the scope of the appended claims.

We claim:

1. A process for the treatment of aqueous sugar juice containing a mixture of ketose and aldose sugars for separating the ketose sugar therefrom comprising:

preparing a reactive hydro-organic medium containing water by mixing the sugar juice with an active methylene ketone compound, a catalyst consisting essentially of a calcium salt, and an alcohol selected from the group consisting of ethanol and methanol, heating said medium to a temperature between 40° C. and the reflux temperature of said medium for a period of about four to eight hours for producing a condensation of the ketone compound and the aldose with the formation of corresponding furanic polyols, cooling said medium to precipitate the furanic polyols, and separating the resulting precipitate from the residual liquid medium containing the ketose.

2. A method as in claim 1, and including adjusting the quantity of said alcohol with respect to the quantity of water in said medium so that the proportion of said alcohol in the water by weight is approximately between 80 and 95%.

3. A method as in claim 1 and including providing the active methylene ketone compound in excess of the stoichiometric proportions with respect to the aldose sugar contained in the sugar juice.

4. A method as in claim 1 and including providing said catalyst in molar proportions of between 1 and 6 with respect to the aldose sugar contained in the sugar juice.

5. A method as in claim 1 and wherein said active methylene ketone compound is ethyl or methyl acetylacetate.

6. A method as in claim 1 and wherein said active methylene ketone compound is acetylacetone.

7. A method as in claim 1 and wherein the calcium salt is calcium chloride.

8. A method as in claim 1 and including adding water to the medium after the condensation for enhancing the precipitation of the furanic polyols.

9. A method as in claim 1 and wherein the separating is accomplished by filtering.

10. A method as in claim 1 and wherein said sugar juice consists essentially of an aqueous mixture of fructose and glucose.

11. A method as in claim 1 and wherein said aldose is glucose and said ketose is fructose.

* * * * *